United States Patent [19]
Lievan

[11] Patent Number: 6,097,485
[45] Date of Patent: Aug. 1, 2000

[54] MICROCHIP OPTICAL TRANSPORT TECHNOLOGY FOR USE IN A PERSONAL FLOW CYTOMETER

[75] Inventor: Bonnie A. Lievan, Brookings, S. Dak.

[73] Assignee: Integrated Waveguides, Inc., Brookings, S. Dak.

[21] Appl. No.: 09/264,178

[22] Filed: Mar. 8, 1999

Related U.S. Application Data

[60] Provisional application No. 60/077,255, Mar. 9, 1998.

[51] Int. Cl.[7] ............................ G01N 21/00; G01N 30/02
[52] U.S. Cl. ........................... 356/338; 356/337; 356/73; 356/317; 422/108; 422/70; 422/68.1; 422/81
[58] Field of Search .................................. 356/337, 338, 356/317, 244, 246, 72, 73, 39; 422/70, 68.1, 108, 81

[56] References Cited

U.S. PATENT DOCUMENTS

| | | | |
|---|---|---|---|
| 5,100,627 | 3/1992 | Buican et al. | 356/244 |
| 5,457,526 | 10/1995 | Kosaka | 356/73 |
| 5,677,196 | 10/1997 | Herron et al. | 356/317 |
| 5,935,522 | 8/1999 | Swerdlow et al. | 422/70 |

OTHER PUBLICATIONS

"Organic–inorganic materials or Integrated optoelectronic" By M.A. Fardad and Fallahi Electronics Letters Oct. 1st, 1998 vol. 34 No. 20.

"Modular concept of a laboratory on a chip for chemical and biochemical analysis" By Gert Blankenstein & Ulrik Darling Larsen Biosensors & Bioelectronics vol.13, No. 3–4, pp. 427–438, 1998.

"Application of Precise Fluid Control on Microchips" Category: Biosensors By J. Michael Ramsey, Andrew G. Hadd, and Stephen C. Jacobson 1997 International Conference on Solid–State Sensors and Actuators pp. 919–921.

"Micro–and Nanofabricated Structures and Devices for Biomedical Environmental Applications" By Paul L. Gourley and Abraham Katzir SPIE vol. 3258. 0277–786X/98/$10.00 pp. 216–223.

"Abstract of Silicon microchannel optical flow cytometer" United States Patent Altendorf, et al. 5,726,751 Mar. 10, 1998 Inventors: Eric H. Altendorf and Paul Yager p. 1 of 12 and p. 1 of 2.

"Monolithic integrated microgratings and photodiodes for wavelength demultiplexing" By T. Suhara, Y. Handa a) H. Nishihara, and J. Koyama Department of Electronics, Faculty of Engineering, Osaka University 2–1, Yamada–ika, Suita, Osaka, 565 Japan pp. 120–122.

*Primary Examiner*—Frank G. Font
*Assistant Examiner*—Roy M. Punnoose
*Attorney, Agent, or Firm*—Hogan & Hartson, L.L.P.

[57] ABSTRACT

An ultra-miniature personal flow cytometer (pFCM) for the measurement of laser-induced fluorescence. The pFCM is approximately the size of a fluorescent microscope and includes a miniature optical module onto which the flow cytometry components are coupled. The miniature optical module is closely integrated with a flow cell through which a sample cell stream flows. The advantage of the pFCM is its compact size and efficiency that is made possible due to the unique microchip demultiplexing waveguide utilized in the separation of fluorescent wavelengths. The microchip demultiplexing waveguide is wholly contained in a tiny microchip consisting of a wave channel layer, a buffer layer, a substrate layer, and a plurality of micrograting filters. Photodetectors may either be coupled to the microchip demultiplexing waveguide by individual fiber optic members or incorporated into the wave channel layer in a photodiode array. The pFCM has wide ranging applications, but in particular is very useful in the analysis of sperm chromatin structure assay (SCSA) because of its small size and simplicity in operating.

48 Claims, 2 Drawing Sheets

MICROCHIP OPTICAL TRANSPORT TECHNOLOGY FOR USE IN A PERSONAL FLOW CYTOMETER

CROSS-REFERENCE TO RELATED APPLICATION

This application claims the benefit of U.S. Provisional Application No. 60/077,255, filed Mar. 9, 1998, which application is specifically incorporated herein, in its entirety, by reference.

BACKGROUND OF THE INVENTION

1. Field of the Invention

The present invention relates to flow cytometers, and more specifically, to an ultra-miniature personal flow cytometer (pFCM) for the measurement of laser-induced fluorescence through microchip optical transport technology.

2. Description of Related Art

Optically based instrumentation is the mainstay of analytical and industrial-process equipment. Several analytical techniques have evolved from the original first generation large optical components to second generation microchip-based components. However, there remains certain technology areas, including flow cytometry, where both established and new applications lack microchip-based instrumentation, due to the absence of a microengineered approach to the specific optical requirements.

Flow cytometry is a powerful technique for discovering the optical characteristics of microscopic biological particles (e.g., cells or organelles), with widespread applications including immunology, genetics, microbiology and oncology. Optical flow cytometers use optical parameters such as light scatter and fluorescence to detect physical and chemical properties of the particles. For measurement, particles are arranged in single file, typically by hydrodynamic focussing within a sheath fluid, and are interrogated by a light beam (usually laser) as they flow through the beam. Every cell passing through the laser beam scatters light so that light scatter can be used in conjunction with fluorescence probes to discriminate between stained and unstained cells within a sample. Light scatter is sensitive to cell size, shape, and refractive indices of the plasma membrane and internal structures within the cell. Fixatives and stains change refractive indices and thus affect light scatter. The sensitivity of light scatter to all these parameters is dependent on the scattering angle, the shape of the illuminating beam, and the solid angle over which the light is collected. Scattered light is measured in a near forward direction by a photodetector. In addition, a second photodetector is often positioned at 90° to the forward scattering direction to collect large angle light scatter and fluorescence emitted by the particles.

Fluorescence is light remitted following absorption to light energy. Although a wide range of organic molecules found within cells are capable of fluorescence, flow cytometry generally depends on the addition of specific fluorescent dye molecules. Common fluorescence techniques rely on the dye binding specifically to some cellular component, such as DNA, which can then be measured by the fluorescence signal. Thermodynamics requires that emitted light be at a lower energy level than the exciting light that induces the fluorescence. Therefore, fluorescence must be at a longer wavelength, than the exciting light, and this separation in wavelength is known as the Stokes shift. The Stokes shift enables the exciting and emitted light to be separated by optical filters so that the fluorescence can be measured in spite of a huge background of exciting light. The magnitude of the Stokes shift varies with different fluorescent molecules, and it is therefore possible to separate the fluorescence emitted by different molecules excited by the same light source. The simultaneous measurement of (several) fluorescent compounds, together with light scattering measurements (at one or more angles) on single cells illustrates the potential of flow cytometry for multi-parameter data.

Generally, lenses are used to collect fluorescence to transmit it to the photodetectors. Light shielding techniques, including placing apertures in the image plane of the collection lens, are employed to prevent most of the forward scattered light and stray light from reaching the fluorescence photodetector(s). Nevertheless, the lens will also collect some scattered light and stray light. Therefore, optics which limit the bandwidth of light reaching the photodetector are employed. This is often accomplished by optical filters that either absorb or reflect light outside the spectral region of interest. The photodetector used to measure the forward scatter is typically a photodiode, such as a solar cell, while the fluorescence detector (90° scatter) is generally a photomultiplier tube (PMT) because of the higher gain available with these tubes.

Prior art flow cytometers are much larger and more complicated than the pFCM of the present invention. This size translates to cost and complexity. The units generally take up a large amount of bench real estate and are relatively delicate. Thus, there exists a need for a miniaturized flow cytometry system for laboratory use that provides portability, simplicity, increased efficiency, and reduced cost.

It is therefore an object of this invention to provide a miniature pFCM for use in analyzing cell structures.

It is another object of this invention to provide microchip optical transport technology for use in a pFCM.

It is still a further object of this invention to provide a miniature optical module consisting of several components including a microchip demultiplexing waveguide to separate visible fluorescent wavelengths.

SUMMARY OF THE INVENTION

In accordance with the teachings of the present invention, an ultra-miniature pFCM for the measurement of laser-induced fluorescence through microchip optical transport technology is provided. The present invention encompasses a complete system in a compact package for the analysis of cells and other biological particles. This system includes a miniature optical module equipped with microchip optical transport technology to quickly and correctly detect and distinguish fluorescent wavelengths for the analysis of cell parameters and characteristics.

The entire miniaturized pFCM of the present invention is approximately the same size as a fluorescent microscope. The miniature optical module, on a single rectangular card, is configured with a hole in a central region, providing a pathway for a fluidic sample cell stream. A miniature laser light source is positioned to intersect the cell stream. A sensing device such as a photodiode is positioned directly across from the laser light source to receive the forward angle light scatter (FALS). A collection lens is stationed approximately 90° from the laser light source to focus the side angle light scatter (SALS) and fluorescence into a fiber optic structure. The collected light is transported to a microchip demultiplexing waveguide, where the fluorescent light is separated into a number of fluorescence channels. The filtered and separated fluorescent light is detected by a plurality of photodiodes, amplified and sent to a digitizer where the signals are converted and sent to a host computer for analysis.

The microchip demultiplexing waveguide is in the form of a microchip and consists of a wave channel layer, a buffer layer, a substrate layer, and a plurality of micrograting filters. The wave channel layer is used to facilitate the transport of the light through the microchip demultiplexing waveguide, and thus, must be transparent to the visible wavelengths. In the preferred embodiment, the wave channel layer is made of a sol-gel material that has the property of being transparent to fluorescent light in the 400 nm–800 nm range (visible light). The wave channel layer further includes a subset of wave channels particular for each wavelength to be separated; thus, in a presently preferred embodiment, three separate channels are present in the wave channel layer to accommodate the three desired wavelengths (488 nm, 530 nm and 640 nm) after they are separated. The micrograting filters, which are etched into the wave channel layer by electron beam, function to separate a narrow band of wavelengths from a multi-spectral beam. The substrate layer is made of a material such as silicon or sapphire, in wafer form, to provide a solid base for the microchip demultiplexing waveguide. The buffer layer is useful in preventing light leakage from the microchip demultiplexing waveguide into the substrate layer and is composed of silica ($SiO_2$). The advantages of the microchip demultiplexing waveguide are its small dimensions and high efficiency.

While the miniaturized pFCM is useful in a multitude of applications, the application in mind during its inception was for use in analysis of a Sperm Chromatin Structure Assay (SCSA). In particular, studies have shown a strong correlation between abnormal chromatin structure, defined as the susceptibility of sperm DNA to denaturation in situ, and male factor infertility. The SCSA is prepared using the fluorochrome acridine orange (AO) to detect the susceptibility to DNA denaturation. Because acridine orange fluoresces at only a few different wavelengths, a small number of photodiodes are all that is required for the microchip demultiplexing waveguide. Thus, the miniature pFCM is an ideal system for analysis of SCSA due to its simplicity and effectiveness.

A more complete understanding of the microchip optical transport system for use in a pFCM will be afforded to those skilled in the art, as well as a realization of additional advantages and objects thereof, by a consideration of the following detailed description of the preferred embodiment. Reference will be made to the appended sheets of drawings that will first be described briefly.

DETAILED DESCRIPTION OF THE PREFERRED EMBODIMENT

The present invention satisfies the need for an apparatus to detect and distinguish fluorescent wavelengths for the purpose of analyzing cell structure and cell characteristics using equipment that is microengineered for broad applications and cost effectiveness. This is accomplished by the miniaturized pFCM consisting of a miniature optical module, including a pathway through which a sample cell stream flows and optical transport technology to convey, separate and detect visible fluorescent wavelengths.

Figure 1:
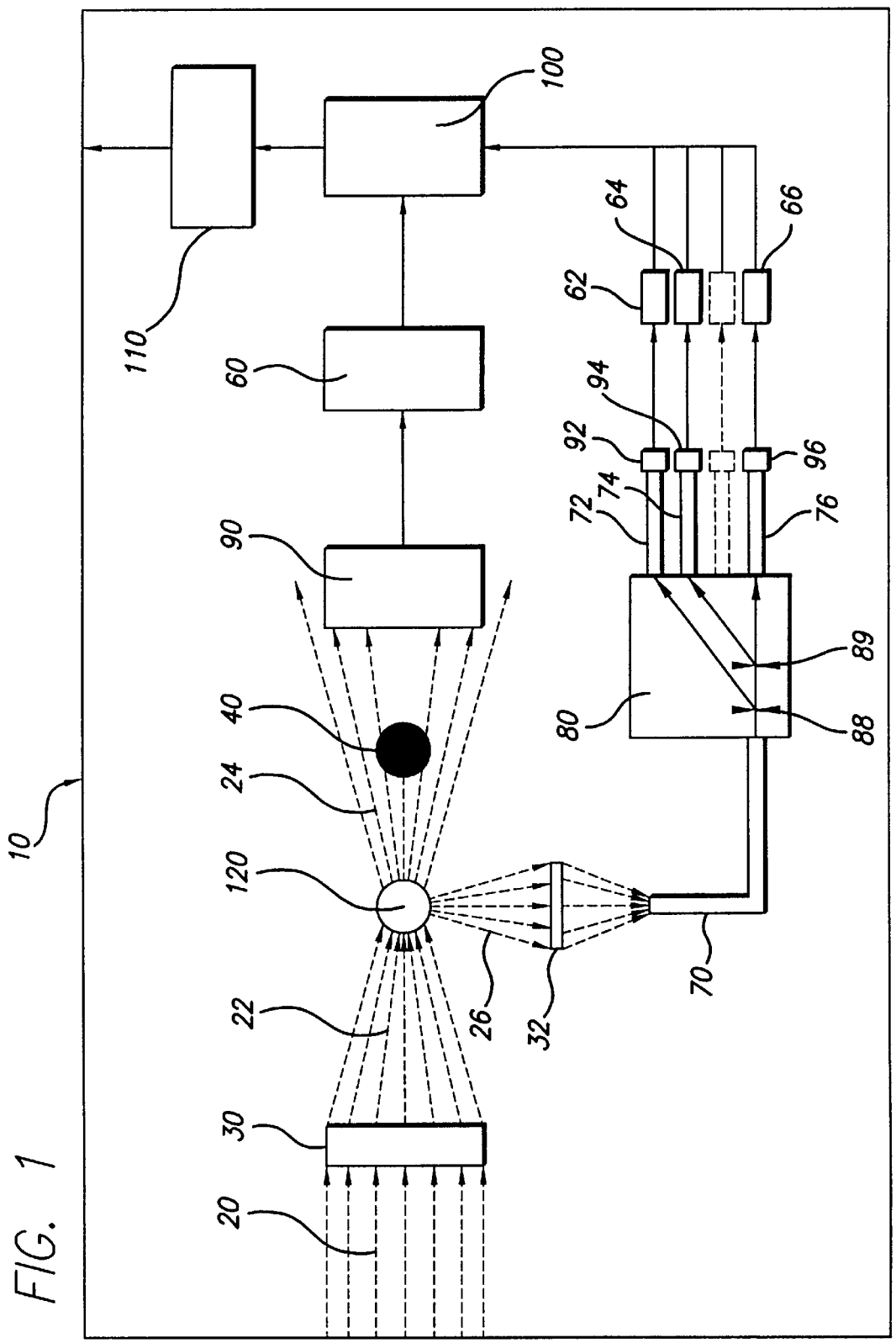
FIG. 1 is a top view of the miniature pFCM board of the present invention.

Referring to FIG. 1, a miniature optical module 10 is shown. In the preferred embodiment, the miniature optical module 10 is rectangular in shape (approximately 12 cm×20 cm or smaller) and contains all of the necessary optics on a single card. A hole 120, providing a pathway for a fluidic sample cell stream 130 (shown in FIG. 3), runs through the miniature optical module 10. A laser light source (not shown) provides a beam 20 of light that impinges on the sample cell stream 130 after passing through a focussing lens 30. The lens 30 and the other components are attached to the miniature optical module 10. A typical laser to be used with the pFCM is an argon ion laser operating at 488 nm, which is a wavelength useful for excitation of AO. Those of ordinary skill in the art will appreciate that the precise type of laser should be matched to the application. That is, if red-excited dyes (such as cyanine dyes) are used then a neon helium or solid state diode laser is appropriate. In fact, the optimal laser for a pFCM, in terms of size and ruggedness, is a solid state diode laser. Such a diode laser could easily be accommodated on the optical module 10 with no increase in module size. Unfortunately, commercial solid state lasers of the correct wavelength to excite AO are just becoming available and must be considered experimental at this time.

Therefore, the 488 nm wavelength needed by AO currently requires an argon ion laser. It is expected that this will be replaced by a solid state diode laser within the next few years thereby allowing an even smaller pFCM. After the focussing lens 30 converges the laser light 20 onto the sample cell stream 130, light is scattered by the cells. Cells or other particles in the core fluid 137 of the sample cell stream 130 emit fluorescence light and scatter light in all directions. An obscuration bar 40, is positioned across from the laser light source to the protect photodiode 90 from the direct excitation beam. The obscuration bar 40 can consist of a black wire approximately equal to the diameter of the sample cell stream 130 and is attached to the miniature optical module 10. Light scattered in a forward direction (i.e. approximately 180° from the incoming laser beam 20), is collected by the photodiode 90 which is also attached to miniature optical module 10. Typically, a silicon photodiode or solar cell is used to detect forward scatter light because the scattered light is so bright. The photodiode 90 produces small currents in response to the incident light. An operational amplifier 60 is included on the miniature optical module 10 to convert the small currents to large voltages, which are sent to an analog/digital converter 110. In an alternate embodiment, the operational amplifier 60 sends the signal to multiplexer 100 that accumulates signals from various sources and transmits them sequentially to the analog/digital converter 110.

Light scattered in a 90° direction contains the fluorescence signals used to analyze the cells. This fluorescence emission is gathered by a collection lens 32. The collection lens 32 transmits the fluorescence light through a multimode fiber optic member 70 which transports the fluorescence light to microchip demultiplexing waveguide 80. This waveguide 80 replaces the large optical bench traditionally found in flow cytometers. The microchip demultiplexing waveguide 80 filters and separates wavelengths of fluorescence light using micrograting filters 88 and 89. The separated wavelengths are directed by separate multimode optical fibers 72, 74 and 76 to photodiodes 92, 94 and 96 respectively. Photodiodes 92, 94 and 96 convert the optical signals into electrical signals which are sent to operational amplifiers 62, 64 and 66 respectively, before being transmitted to analog/digital converters 110 (or alternately, first to a multiplexer 100). The analog/digital converters 110 send the converted signals to a host computer (not shown) where the results of the optical cell analysis can be assembled and manipulated.

The miniature optical module 10 performs virtually all of the optical and electronic functions of a traditional flow cytometer. With the addition of a laser diode even the light source is integral to the module 10. The fluidics are separate from the module 10 except that the flow cell is positioned or linked to the module 10 so that the sample flow actually passes through the module 10. As mentioned above, the module 10 is very small; however, sources of sheath fluid (say one liter) and a waste container require considerable volume. These as well as necessary tubing and valves dictate that the whole unit be about the size of a fluorescence microscope (about 52–62 cm×46–56 cm). It will be appreciated that if the sheath source and/or the waste bottle is placed in a separate housing, the pFCM can be much smaller than these dimensions. It is contemplated by the inventor that a source of pressurized gas (say nitrogen) is used as the pumping force for the fluidics. A relatively small compressed gas cylinder (separate from the unit) would operate the fluidics for an extended period of time. Although the drawings show the sample stream actually passing through an aperture in the optical module 10, there is no reason that the optical module 10 could not be oriented parallel to the flow cell with the sample stream being essentially parallel to the surface of the module 10. The important point is that the optical module 10 be closely integrated with the flow cell so that light transmission distances be kept minimal and so that the entire unit be kept as small as possible.

Figure 2:
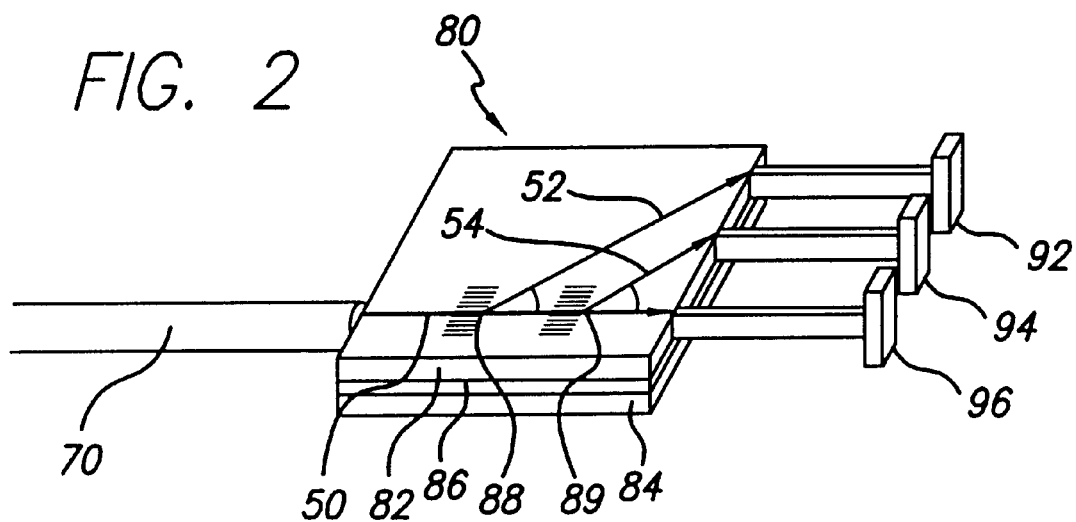
FIG. 2 is an enlarged perspective view of the microchip demultiplexing waveguide of the present invention.

Referring to FIG. 2, the microchip demultiplexing waveguide 80 is illustrated in greater detail. The microchip demultiplexing waveguide 80 is the functional heart of the miniature optical module 10, functioning to separate optical wavelength bands by means of transmissive micrograting filters 88 and 89. As shown, and in a preferred embodiment, the microchip demultiplexing waveguide 80 utilizes two filters 88 and 89 of the transmission grating type to separate the fluorescent light into two wavelength bands. It is possible, however, to produce a plurality of different wavelength bands using the same technique with one grating filter per wavelength band. In an alternate embodiment the reflection grating configuration is used, wherein the incoming wavelengths are reflected to photodiodes located approximately normal to the incoming light beam.

The micrograting filters 88 and 89 are etched into microchip demultiplexing waveguide 80 through a computer-controlled electron beam writing process, using a scanning electron microscope to match the periodicity of the narrow band of wavelengths desired (in the preferred embodiment this includes 488 nm, 530 nm and 640 nm). The micrograting filters 88 and 89 have the same slant angle $\theta_B$ but different periods. Each grating deflects a guided wave according to the following equation (the Bragg condition):

$$2\Lambda\sin\theta_B = \lambda/n_e$$

where $\Lambda$ is the grating period, $\lambda$ is the wavelength in free space, and $n_e$ the effective index of refraction of the guided wave. The migrograting filters 88 and 89 can be designed based on coupled wave analysis by determining the grating period using the above equation. The microchip demultiplexing waveguide 80 further consists of wave channel layer 82, a buffer layer 86 and a substrate layer 84. In a preferred embodiment, the wave channel layer 82 is made of a sol-gel material, which is composed of either silicon nitride and silicon, or organic silicate and is 1–10 $\mu$m thick. The sol-gel matrix is chosen for its transparent properties above 250 nm, meaning that it is transparent to the visible fluorescent wavelengths between 400 and 800 nm that are used with the present invention. Sol-gel is produced by a method, which makes glass without using a melting process. Organic compounds such as alcoholates of silicon, sodium or calcium are mixed with water, wherein the compounds hydrolyze to yield an alcohol and metal (or semi-metal in the case of silicon) which metal undergoes further reaction with the water. This process creates a structure where the metallic atoms are bonded to oxygen atoms in an irregular non-crystalline network, thus forming a gel. Low-temperature treatment then turns the gel into an inorganic glass that is used in the wave channel layer 82. The substrate layer 84 consists of a wafer backing for the chip made of silicon or sapphire as is customary in the art. The buffer layer 86 separates the wave channel layer 82 and the substrate layer 84 for the prevention of light leakage and is made of silica approximately 2–3 $\mu$m thick. The specific fabrication process for the microchip demultiplexing waveguide is as follows:

The sol-gel organic-inorganic material is synthesized by mixing methacryloxy propyl trimethoxysilane (80 mol %), aluminum butoxide (20 mol %), and hydrogen chloride catalyzed water in a molar ration of 1:1:3. A few drops of Darocur, (hydroxy methyl propiophenone) are added as a catalyst for photopolymerization for the methacryloxy groups after film deposition. The homogeneous solution of composite is aged approximately 24 hours while being continuously stirred. The sol is then diluted and dispensed through a 0.1 $\mu$m filter onto a silicon wafer with a 3 $\mu$m thermally grown silica buffer layer, and spin coated at 2000 rpm for 30 s. The coated planar gel film is soft baked at 100° C. for 5 min, and is exposed for 25 min to UV light through a mask using a mask aligner with 275 W output power. The mask pattern consists of straight channels and 1×2 splitters with 3 5 $\mu$m opening widths (±0.25 $\mu$m). The photoinscribed channels are thereafter developed in propanol for a few minutes to dissolve the non-photopolymerized material, followed by hard baking at 100 to 170° C. in a vacuum for several hours.

The microchip demultiplexing waveguide 80 is cleaved along the edge so that the fiber optic member 70 can be directly coupled to the microchip demultiplexing waveguide 80 near the wave channel layer 82 for transmission of the wavelength bands. The wave channel 82 includes a subchannel 50, which transports the light from the multimode fiber optic member 70 through the microchip demultiplexing waveguide 80 to intersect the micrograting filters 88 and 89. The wave channel 82 further includes subchannels 52 and 54, which are small ridges (3×3 $\mu m^2$ or 5×3 $\mu m^2$) that transport the separated wavelength to the edge of microchip demultiplexing waveguide 80. The wavelength band (here 488 nm) that is not separated by the micrograting filters 88 and 89 continues on along the subchannel 50 to the edge of microchip demultiplexing waveguide 80. The 488 nm wavelength band represents wide angle scattered light from the argon ion laser and is indicative of cellular granularity. Coupled to the edge of microchip demultiplexing waveguide 80 opposite of the incoming emission light are multimode optical fibers 72, 74 and 76, which are spaced approximately 250 $\mu$m apart. These multimode optical fibers carry the separated wavelengths to photodiodes 92, 94 and 96 for detection.

In the preferred embodiment, the cells stained with AO will fluoresce at 530 nm (green) and 640 nm (red) and three photodiodes 92, 94 and 96 will be necessary to detect these two wavelengths as well as the 488 nm (blue) right angle light scatter. However, microchip demultiplexing waveguide 80 can also be configured to measure other commonly used fluorochromes for other applications with wavelength bands including 464–512 nm, 494–546 nm, 546–604 nm and 634–700 nm. Thus, in the preferred embodiment, the incoming wave from fiber optic member 70 is demultiplexed into wavelength band components by micrograting filters 88 and 89, and the wavelength bands are transmitted by multimode optical fibers 72, 74 and 76 to each photodiode 92, 94 and 96 respectively according to their wavelengths. Other types of photodetectors can be substituted but optimal results result from detectors that are small in size as compared to the waveguide 80. The multimode optical fibers 72, 74 and 76 can be longer or shorter or even eliminated depending on the precise configuration and the type of photodetector.

Figure 3:
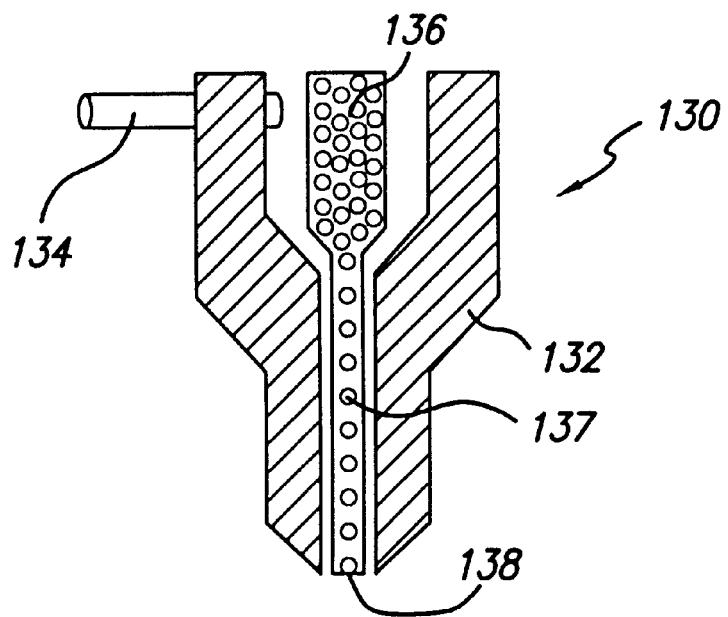
FIG. 3 is a cross-sectional view of the sample cell stream of the present invention.

Turning now to FIG. 3, where the sample cell stream 130 is shown. The sample cell stream 130 consists of a flow chamber 132, a sheath fluid 134, cells 136 and a core sample fluid 137 in which the cells are suspended. During analysis cells travel through the low chamber 132 at a rate of approximately 250 cells/s. The sheath fluid 134 provides a laminar flow for the core fluid 137. The diameter of cells 136 in the sample fluid 137 is gradually reduced by hydrodynamic focussing downstream from the injection point to provide a single file of cells As shown in FIG. 3, the sample cell stream 130 flows in a downward direction although an upward direction could also be utilized. The single cells in sample fluid 137 pass through the laser light beam 20 at interrogation point 138. Once the cells have been exposed to laser 20, they continue on to a waste tank (not shown).

The miniature pFCM is ideally used in the analysis of sperm chromatin structure assay (SCSA). SCSA data has been correlated with fertility, and evaluations regarding sperm quality can be easily and comprehensively derived from SCSA tests (Evenson, D. P., et al. (1997) Apoptotic Human Ejaculated Sperm Contribute to Infertility; Evenson, D., et al. (1995) Flow cytometry of sperm chromatin structure as related to toxicology and fertility, Seventh International Spermatology Symposium, Cairns, Australia (October), Proceedings). Individual semen samples are stained with AO in two steps, which allows rapid measurements of ratios of cell types present. AO fluoresces green (530 nm) when intercalated into native, double stranded DNA and red (640 nm) when associated with denatured DNA. The AO is useful in simultaneously determining DNA (green) and RNA (red) concentrations. Another use for SCSA is as a toxicology assay for male mammals exposed to toxic environmental substances or stresses or to detect toxic properties of candidate drugs, etc. Because toxic chemicals alter the sperm chromatin structure of mammals, an SCSA test can determine whether or not a mammal has been exposed or whether a given compound is toxic (Wyrobek, A. J., et al. (1997)). Assessment of reproductive disorders and birth defects in communities near hazardous chemical sites. III. Guidelines for field studies of male reproductive disorders, Reproductive Toxicology, vol. 10, no. 5). Ambient heat has also been shown to affect sperm chromatin structure giving rise to SCSA analysis (Sailer, B. L., et al. (1997), Effects of heat stress on mouse testicular cells and sperm chromatin structure as measured by flow cytometry, J Androl, vol. 18, pp. 294–301). The pFCM of the present invention provides a rapid, sensitive, quantitative, statistically sound and objective instrumentation for the analysis of SCSA.

Having thus described a preferred embodiment of the microchip optical transport technology system for use in a pFCM, it should be apparent to those skilled in the art that certain advantages of the within system have been achieved. It should also be appreciated that various modifications, adaptations, and alternative embodiments thereof may be made within the scope and spirit of the present invention. For example, while the pFCM has been illustrated to apply to the analysis of SCSA, it should be apparent that the inventive concepts described above would be equally applicable to many other applications for which standard flow cytometers are used. The invention is further defined by the following claims.

What is claimed is:

1. A cell analysis apparatus comprising:

a unitary optical module;

a microchip demultiplexing waveguide integral to said optical module, a flowing sample stream closely integrated with said optical module;

a light source for generating a light beam disposed so that the light beam interacts with the fluidic sample stream adjacent to an opening;

a plurality of photodetectors integral to said optical module;

means for collecting light scattered and emitted from the fluidic sample stream in response to the light beam;

means for transmitting collected light to the microchip waveguide; and means for transmitting light from the microchip waveguide to the photodetectors.

2. The cell analysis apparatus of claim 1, wherein the flowing sample stream passes through an aperture in said optical module.

3. The cell analysis apparatus of claim 1, further comprising a lens device disposed between said opening and said light source.

4. The cell analysis apparatus of claim 1, wherein said microchip demultiplexing waveguide further comprises:

a substrate layer;

a buffer layer disposed on top of said substrate layer;

a wave channel layer disposed on top of said buffer layer; and a plurality of micrograting filters disposed within said wave channel layer.

5. The cell analysis apparatus of claim 4, further comprising:

a photodiode array disposed in contact with said wave channel layer of said microchip demultiplexing waveguide; and a plurality of operational amplifiers coupled to said photodiode array.

6. The cell analysis apparatus of claim 1, wherein the means for transmitting collect light to the microchip waveguide comprises at least one fiber optic member and wherein the means for transmitting light from the microchip waveguide comprises at least one fiber optic member.

7. The cell analysis apparatus of claim 1, wherein at least one of said photodetectors is a photodiode.

8. The cell analysis apparatus of claim 6, wherein at least one photodiode is coupled to the microchip waveguide.

9. The cell analysis apparatus of claim 1, further comprising a plurality of operational amplifiers coupled to said photodetectors.

10. The cell analysis apparatus of claim 9, further comprising a multiplexer coupled to said operational amplifiers.

11. The cell analysis apparatus of claim 6, further comprising a multiplexer.

12. The cell analysis apparatus of claim 10, wherein said multiplexer is coupled to an analog/digital converter.

13. The cell analysis apparatus of claim 11, wherein said multiplexer is coupled to an analog/digital converter.

14. The cell analysis apparatus of claim 4, wherein said wave channel layer is made of a sol-gel material.

15. The cell analysis apparatus of claim 4, wherein said wave channel layer further comprises a plurality of subchannels.

16. The cell analysis apparatus of claim 4, wherein said micrograting filters are etched into said wave channel layer through a computer-controlled electron beam writing process.

17. The cell analysis apparatus of claim 4, wherein each one of said micrograting filters has the same slant angle but different periods.

18. The cell analysis apparatus of claim 4, wherein said micrograting filters are in a transmission grating configuration.

19. The cell analysis apparatus of claim 4, wherein said micrograting filters are in a reflection grating configuration.

20. The cell analysis apparatus of claim 1, wherein said unitary optical module comprises a card which is between 10 cm and 14 cm wide, and 18 cm and 22 cm long.

21. The cell analysis apparatus of claim 1, further comprising a housing which is between 52 cm and 62 cm wide, between 46 cm and 56 cm deep, and between 72 cm and 92 cm tall.

22. The cell analysis apparatus of claim 1, further comprising a host computer coupled to said photodetectors by means of an analog/digital converter.

23. An analysis system for detecting cell characteristics comprising:
   a fluidic cell stream for providing cells to be analyzed;
   light means for emitting light to illuminate said cells in said fluidic cell stream;
   an optical module comprising a microchip demultiplexing waveguide for separating different wavelengths of said light from said illuminated cells, said optical module closely integrated with said fluidic cell stream;
   detection means for detecting said different wavelengths separated by said waveguide; and
   amplifying means coupled to said detection means and said separation means for amplifying signals.

24. The cell analysis system of claim 23, wherein said light means is an argon ion laser.

25. The cell analysis system of claim 23, wherein said detection means is a plurality of photodiodes.

26. The cell analysis system of claim 23, wherein said microchip demultiplexing waveguide comprises:
   a substrate layer;
   a buffer layer disposed on top of said substrate layer;
   a wave channel layer disposed on top of said buffer layer; and
   a plurality of micrograting filters disposed within said wave channel layer.

27. The cell analysis system of claim 26, wherein the detection means are coupled to said microchip demultiplexing waveguide by optical fiber members.

28. The cell analysis system of claim 26, wherein said wave channel layer is made of a sol-gel material.

29. The cell analysis apparatus of claim 26, wherein said wave channel layer further comprises a plurality of subchannels.

30. The cell analysis system of claim 26, wherein said micrograting filters are etched into said wave channel layer through a computer-controlled electron beam writing process.

31. The cell analysis system of claim 26, wherein each one of said micrograting filters has the same slant angle but different periods.

32. The cell analysis system of claim 26, wherein said micrograting filters are in a transmission grating configuration.

33. The cell analysis system of claim 26, wherein said micrograting filters are in a reflection grating configuration.

34. The cell analysis system of claim 23, further comprising a housing for covering and fastening components of said system.

35. The cell analysis system of claim 34, wherein said housing is between 30 cm and 62 cm wide, between 24 cm and 56 cm deep, and between 60 cm and 92 cm tall.

36. The cell analysis system of claim 23, further comprising computational means for assembling and displaying information gathered from said scattered light signals.

37. An ultra-miniature optical module closely integrated with a flowing sample stream, the ultra-miniature optical module comprising:
   a collection lens disposed to collect light from a flowing sample stream when the flowing sample stream is illuminated;
   a fiber optic member operationally coupled to said collection lens;
   a microchip demultiplexing waveguide optically coupled to said collection lens; and
   a photodetector operationally coupled to said waveguide.

38. The ultra-miniature optical module of claim 37, wherein said microchip demultiplexing waveguide further comprises:
   a substrate layer;
   a buffer layer disposed on top of said substrate layer;
   a wave channel layer disposed on top of said buffer layer; and
   a plurality of micrograting filters disposed within said wave channel layer.

39. The ultra-miniature optical module of claim 38, further comprising a photodiode array disposed in contact with said wave channel layer.

40. The ultra-miniature optical module of claim 38, wherein said wave channel layer is made of a sol-gel material.

41. The ultra-miniature optical module of claim 38, wherein said wave channel layer further comprises a plurality of subchannels.

42. The ultra-miniature optical module of claim 38, wherein said micrograting filters are etched into said wave channel layer through a computer-controlled electron beam writing process.

43. The ultra-miniature optical module of claim 38, wherein each one of said micrograting filters has the same slant angle but different periods.

44. The ultra-miniature optical module of claim 38, wherein said micrograting filters are in a transmission grating configuration.

45. The ultra-miniature optical module of claim 38, wherein said micrograting filters are in a reflection grating configuration.

46. The ultra-miniature optical module of claim 38, wherein said micrograting filters are in a transmission grating configuration.

47. The ultra-miniature optical module of claim 37, further comprising a plurality of operational amplifiers coupled to said detectors.

48. The ultra-miniature optical module of claim 37, further comprising:

a plurality of fiber optic members coupled to said microchip demultiplexing waveguide; and a plurality of detectors coupled to said fiber optic members.

\* \* \* \* \*